(12) United States Patent
Zanella et al.

(10) Patent No.: US 7,749,555 B2
(45) Date of Patent: Jul. 6, 2010

(54) MODIFICATION OF CHEMICAL FORCES OF BONE CONSTRUCTS

(75) Inventors: John M. Zanella, Cordova, TN (US); Sean M. Haddock, Memphis, TN (US); Catherine E. Taylor, Northeast Fridley, MN (US); Kathryn J. Kitching, London (GB)

(73) Assignees: Medtronic, Inc; Warsaw Orthopedic, Inc.

( * ) Notice: Subject to any disclaimer, the term of this patent is extended or adjusted under 35 U.S.C. 154(b) by 411 days.

(21) Appl. No.: 11/339,781

(22) Filed: Jan. 25, 2006

(65) Prior Publication Data

US 2007/0173950 A1    Jul. 26, 2007

(51) Int. Cl.
*B05D 3/04*    (2006.01)
*A61F 2/28*    (2006.01)

(52) U.S. Cl. .................. 427/2.26; 623/23.63; 623/919; 435/402

(58) Field of Classification Search ............... 623/23.63, 623/919, 923
See application file for complete search history.

(56) References Cited

U.S. PATENT DOCUMENTS

| | | | | |
|---|---|---|---|---|
| 5,236,456 | A * | 8/1993 | O'Leary et al. | 623/23.63 |
| 5,645,591 | A * | 7/1997 | Kuberasampath et al. | 424/423 |
| 6,033,582 | A | 3/2000 | Lee et al. | |
| 6,190,412 | B1 * | 2/2001 | Lee et al. | 623/16.11 |
| 6,294,187 | B1 * | 9/2001 | Boyce et al. | 424/422 |
| 6,299,650 | B1 * | 10/2001 | Van Blitterswijk et al. | 623/23.63 |
| 6,458,168 | B1 | 10/2002 | Lagrange et al. | |
| 6,511,509 | B1 | 1/2003 | Ford et al. | |
| 6,602,296 | B1 * | 8/2003 | Day et al. | 623/23.49 |
| 6,843,807 | B1 * | 1/2005 | Boyce et al. | 623/23.51 |
| 6,899,107 | B2 | 5/2005 | Lewandrowski et al. | |
| 2003/0009235 | A1 * | 1/2003 | Manrique et al. | 623/23.63 |
| 2003/0149437 | A1 * | 8/2003 | Livne et al. | 606/76 |
| 2004/0098135 | A1 * | 5/2004 | Stone et al. | 623/23.63 |
| 2004/0228899 | A1 * | 11/2004 | Lee et al. | 424/423 |
| 2005/0163816 | A1 | 7/2005 | Agrawal et al. | |

FOREIGN PATENT DOCUMENTS

WO    2005074530    8/2005

OTHER PUBLICATIONS

Research Disclosure No. 483136, published Jul. 2004.*
Nayab et al., "Effects of calcium ion implantation on human bone cell interaction with titanium," Biomaterials (Aug. 2005), Vo.: 26, No. 23, pp. 4717-4727.
Maendl et al., "Plasma immersion ion implantation. New technology for homogeneous modification of the surface of medical implants of complex shapes," Biomedizineische Technik (Jul. 2000), vol. 45, No. 7, pp. 193-198.
Strates et al., "Skeletal Repair in the Aged: a Preliminary Study in Rabbits", The American Journal of the Medical Sciences, Oct. 1988, vol. 296, No. 4, pp. 266-269.
Urist et al., "Lipids Closely Associated with Bone Morphogenetic Protein (BMP) . . . and Induced Heterotopic Bone Formation . . . ", Connective Tissue Research, vol. 36(1), 1997 OPA, pp. 9-20.
Sammarco et al., "Modern Issues in Bone Graft Substitutes and Advances in Bone Tissue Technology", Foot and Ankle Clinics, 7 (2002), pp. 19-41.
Wozney et al., "Novel Regulators of Bone Formation: Molecular Clones and Activities", Science, vol. 242, pp. 1528-1534, Dec. 16, 1988.
Govender et al., "Recombinant Human Bone Morphogenetic Protein-2 for Treatment of Open Tibial Fractures: a Prospective, Controlled, Randomized Sutdy of Four Hundred and Fifty Patients", the Journal of Bone & Joint Surgery, 84:pp. 2123-2134, 2002, Dec. 2002.

* cited by examiner

Primary Examiner—David H. Willse

(57) ABSTRACT

The present invention relates to a method for enhancing ingrowth of host bone comprising: modifying a bone graft structure to provide an ionic gradient to produce a modified bone graft structure; and implanting the modified bone graft structure. The present invention also relates to a method of enhancing the binding of growth factors and cell cultures to a bone graft structure comprising: applying ex vivo an effective quantity of an ionic force change agent to the surface of a bone graft structure to produce a binding-sensitized bone graft structure; implanting the binding-sensitized bone graft structure into a host bone; and administering to the binding-sensitized bone graft structure a molecule, a cell culture or a combination thereof.

20 Claims, No Drawings

MODIFICATION OF CHEMICAL FORCES OF BONE CONSTRUCTS

FIELD OF THE INVENTION

The present invention relates to methods of making a bone allograft more attractive to host bone cells via surface modifications to the allograft.

BACKGROUND OF THE INVENTION

Numerous approaches are being employed to improve the bone generation and repair cycle (also referred to as the bone repair cascade). Such issues are paramount in the treatment of all bone related defects related to degeneration, injury, infection, malignancy or developmental malformation. In the spinal surgery field, there are several different types of autologous bone graft substitutes that are either currently available or are in various stages of development for use in spine fusion surgery.

Demineralized bone matrix (DBM) is a manufactured product that has been readily available for over ten years. See for example, Grafton Putty (Osteotech, Eaton-town, N.J.); DBX Putty (MTF [Musculoskeletal Transplant Foundation], available through Synthes, Paoli, Pa.); and AlloMatrix Injectable Putty (Wright Medical Technology, Arlington, Tenn.). DBM is prepared by acid extraction of allograft bone, resulting in loss of most of the mineralized component but retention of collagen and noncollagenous proteins, including growth factors. DBM does not contain osteoprogenitor cells, but the efficacy of a demineralized bone matrix as a bone-graft substitute or extender may be influenced by a number of factors, including the sterilization process, the carrier, the total amount of bone morphogenetic protein (BMP) present, and the ratios of the different BMPs present (Strates et al., (1988) *Am J Med Sci*, 296:266-9; Urist et al., (1997) *Connect Tissue Res*, 36:9-20; and Sammarco and Chang, (2002) *Foot Ankle Clin*, 7:19-41). DBM includes demineralized pieces of cortical bone to expose the osteoinductive proteins contained in the matrix. These activated demineralized bone particles are usually added to a substrate or carrier (e.g. glycerol or a polymer). DBM is mostly an osteoinductive product, but lacks enough induction to be used on its own in challenging healing environments such as posterolateral spine fusion.

Allograft bone is a reasonable graft substitute for autologous bone. It is readily available from cadavers and avoids the surgical complications and patient morbidity associated with harvesting autologous bone. Allograft bone is essentially a load-bearing matrix comprised of cross-linked collagen, hydroxyapatite, and osteoinductive Bone Morphogenetic Proteins (BMP). Human allograft tissue is widely used in orthopaedic surgery. Allograft tissue is strong, integrates with the recipient host bone, and can be shaped either by the surgeon to fit the specific defect or shaped commercially by a manufacturing process. Allograft bone is available in two basic forms: cancellous and cortical. Cortical bone is a highly dense structure comprised of triple helix strands of collagen fiber reinforced with hydroxyapatite. The hydroxyapatite component is responsible for the high compressive strength and stiffness of bone while the collagen fiber component contributes to its elastic nature, as well as torsional, shear, and tensile strength. Cortical bone is the main load-bearing component of long bones in the human body.

Many devices of varying shapes and forms can be manufactured from cortical allograft tissue. Surgical implants such as pins, rods, screws, anchors, plates, and intervertebral spacers have all been made and used successfully in human surgery.

Even though allograft has certain advantages over the other treatments, one of the main drawbacks of the allograft treatment is that the ingrowth of the host bone into the grafted bone may take longer than in an autograft. As a result, allograft treatment may be less effective than the autograft. Attempts have been made to overcome these drawbacks by modifying the bone graft's surface. For example, U.S. Pat. No. 6,511,509 discloses a textured graft, wherein the texturing comprises a plurality of closely spaced continuous or discrete protrusions.

U.S. Pat. No. 6,458,168 teaches a graft comprising a combination of two cortical bone portions and a cancellous bone portion located between the cortical bone portions. According to the disclosure, the portions of the composite graft are held together by means other than adhesive and not demineralized.

U.S. Pat. No. 6,899,107 discloses a graft coated with a biopolymer seeded with periosteal cells harvested from either the graft recipient or from an allogenic or a xenogenic source.

U.S. Patent Application Publication No. 20040228899 teaches the use of bone grafts, including allografts, characterized by tartrate-resistant acid phosphatase (TRAP) adsorbed to a porous hydroxyapatite substratum.

Despite the advances recently made in the art, new methods promoting ingrowth of the host bone into the grafted bone are needed to better utilize the advantages of allograft treatment.

SUMMARY OF THE INVENTION

The present invention fills the foregoing need by providing devices, systems and methods for enhancing ingrowth of host bone comprising modifying a bone graft structure to provide an ionic gradient to produce a modified bone graft structure; and implanting the modified bone graft structure. This aspect of the present invention may further provide administering to the modified bone graft structure a molecule, a cell culture or a combination thereof.

In one embodiment of the present invention an ionic force change agent is applied to modify the bone graft structure. According to one embodiment of the invention, the bone graft structure is selected from the group consisting of cortical bone, cancellous bone, subchondral bone and any combination of the various bone tissue types. According to another embodiment, the bone graft structure comprises a composite bone which includes a bone powder, a polymer and a demineralized bone. The ionic force change agent may be a binding agent, which modifies the bone graft structure to bind molecules, such as, for example, growth factors, or cells, such as, for example, cultured cells, or a combination of molecules and cells. In the practice of the invention the growth factors include but are not limited to BMP-2, rhBMP-2, BMP-4, rhBMP-4, BMP-6, rhBMP-6, BMP-7[OP-1], rhBMP-7, GDF-5, LIM mineralization protein, platelet derived growth factor (PDGF), transforming growth factor β (TGF-β), insulin-related growth factor-I (IGF-I), insulin-related growth factor-II (IGF-II), fibroblast growth factor (FGF), beta-2-microglobulin (BDGF II), and rhGDF-5. A person of ordinary skill in the art will appreciate that the invention is not limited to growth factors only. Other molecules can also be employed in the invention. For example, tartrate-resistant acid phosphatase, which is not a growth factor, may also be used in the invention.

If a cell culture is employed, the cells include but are not limited to mesenchymal stems cells, pluripotent stem cells, embryonic stem cells, osteoprogentior cells, osteoblasts, osteoclasts, and any bone marrow-derived cell lines.

In one embodiment of the method of the invention, the ionic forces of the bone graft structure are changed by a one-to-one substitution of the calcium ion with an element selected from the group consisting of lithium, sodium, potassium and cesium ions of hydroxyapatite.

Another aspect of the present invention provides a method of enhancing the binding of molecules and cell cultures to a bone graft structure comprising applying ex vivo an effective quantity of an ionic force change agent to the surface of a bone graft structure to produce a binding-sensitized bone graft structure; and implanting said binding-sensitized bone graft structure into a host bone. It may be desirable to administer to said implanted, binding-sensitized bone graft structure a molecule, a cell culture or a combination thereof all of which are capable of binding to said binding-sensitized bone graft structure. For example, the molecule may be a growth factor such as, for example, BMP-2, rhBMP-2, BMP-4, rhBMP-4, BMP-6, rhBMP-6, BMP-7[OP-1], rhBMP-7, GDF-5, LIM mineralization protein, platelet derived growth factor (PDGF), transforming growth factor β (TGF-β), insulin-related growth factor-I (IGF-I), insulin-related growth factor-II (IGF-II), fibroblast growth factor (FGF), beta-2-microglobulin (BDGF II), and rhGDF-5. Other molecules can also be employed in the invention, such as, for example, tartrate-resistant acid phosphatase, which is not a growth factor.

Cells may also be used instead of or in addition to molecules, such as growth factors. Non-limiting examples of suitable cell types include mesenchymal stems cells, pluripotent stem cells, embryonic stem cells, osteoprogentior cells, osteoblasts and osteoclasts.

DETAILED DESCRIPTION

To aid in the understanding of the invention, the following non-limiting definitions are provided:

The term "allograft" refers to a graft of tissue obtained from a donor of the same species as, but with a different genetic make-up from, the recipient, as a tissue transplant between two humans.

The term "autologous" refers to being derived or transferred from the same individual's body, such as for example an autologous bone marrow transplant.

The term "morbidity" refers to the frequency of the appearance of complications following a surgical procedure or other treatment.

The term "osteoinduction" refers to the ability to stimulate the proliferation and differentiation of pluripotent mesenchymal stem cells (MSCs). In endochondral bone formation, stem cells differentiate into chondroblasts and chondrocytes, laying down a cartilaginous ECM, which subsequently calcifies and is remodeled into lamellar bone. In intramembranous bone formation, the stem cells differentiate directly into osteoblasts, which form bone through direct mechanisms. Osteoinduction can be stimulated by osteogenic growth factors, although some ECM proteins can also drive progenitor cells toward the osteogenic phenotype.

The term "osteoconduction" refers to the ability to stimulate the attachment, migration, and distribution of vascular and osteogenic cells within the graft material. The physical characteristics that affect the graft's osteoconductive activity include porosity, pore size, and three-dimensional architecture. In addition, direct biochemical interactions between matrix proteins and cell surface receptors play a major role in the host's response to the graft material.

The term "osteogenic" refers to the ability of a graft material to produce bone independently. To have direct osteogenic activity, the graft must contain cellular components that directly induce bone formation. For example, a collagen matrix seeded with activated MSCs would have the potential to induce bone formation directly, without recruitment and activation of host MSC populations. Because many osteoconductive scaffolds also have the ability to bind and deliver bioactive molecules, their osteoinductive potential will be greatly enhanced.

The term "patient" refers to a biological system to which a treatment can be administered. A biological system can include, for example, an individual cell, a set of cells (e.g., a cell culture), an organ, or a tissue. Additionally, the term "patient" can refer to animals, including, without limitation, humans.

The term "treating" or "treatment" of a disease refers to executing a protocol, which may include administering one or more drugs to a patient (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols which have only a marginal effect on the patient.

The term "xenograft" refers to tissue or organs from an individual of one species transplanted into or grafted onto an organism of another species, genus, or family.

Aspects of the present invention provide reagents, methods and systems for enhancing ingrowth of host bone. Applicants have found that modifying a bone graft structure to provide an ionic gradient to produce a modified bone graft structure, and implanting the modified bone graft structure results in enhanced ingrowth of host bone.

Depending upon the condition of the patient, new bone ingrowth is accomplished by one or more mechanisms such as osteogenesis, osteoconduction and osteoinduction. It can be appreciated that the needs of a child are different from an aging patient afflicted with osteoporosis. Accordingly, there is no "one size fits all" approach towards optimizing the healing conditions in a patient.

In one aspect, the invention relates to a method of modifying a bone graft structure (also referred to as an implant) in such a way that the original chemical forces naturally present have been altered in such a way as to attract and bind growth factors, other proteins and cells affecting osteogenesis, osteoconduction and osteoinduction.

Intramolecular or intermolecular attractions between atoms are formed through weak chemical forces, which include hydrogen bonds, van der Waals forces, ionic bonds and hydrophobic interactions. These weak forces create bonds that are constantly forming and breaking at physiological temperature and are readily reversible under physiological conditions. The transient bonds between metabolites and macromolecules, and hormones and receptors, and all the other cellular moieties necessary for life are required for biomolecular interactions since rigid, static bonds will inhibit, if not paralyze, cellular activities.

In one aspect of the invention, the implant or bone graft structure is a bone or a part thereof, in its original structure, wherein the chemical forces naturally present are neutral.

In the invention, the bone graft structure is modified in such a way that the original chemical forces naturally present are altered so that the implant attracts and binds proteins, such as, for example, growth factors and cells, including cells from cell cultures. Bone structures include but are not limited to cortical bone, cancellous bone, subchondral bone, or any combination of the various bone tissue types.

The invention provides for a method of enhancing ingrowth of host bone by modifying a bone graft structure, in particular the surface of said bone graft structure, to provide a gradient, implanting the modified bone graft structure, and administering to the modified bone graft structure a molecule, such as, for example, a growth factor, and/or a cell culture. A person of ordinary skill in the art will appreciate that the molecule and/or the cell culture may be administered to the modified bone graft both before and after implanting the modified bone graft into the host bone. An example of a suitable bone graft structure is a cortical bone graft structure such as a bone graft structure in any size and shape. Another non-limiting example of the bone graft structure is a bone composite. According to one embodiment of the invention, the bone composite comprises a bone powder, a polymer and a demineralized bone. In different embodiments of the invention, bone powder content ranged from about 5% to about 90% w/w, polymer content ranged from about 5% to about 90% w/w, and demineralized bone particles content comprised the remainder of the composition. Preferably, the demineralized bone particles comprise from about 20% to about 40% w/w while the polymer and the bone powder comprise each from about 20% to about 60% w/w of the composition. The bone graft structures of the present invention include those structures that have been modified in such a way that the original chemical forces naturally present have been altered to attract and bind molecules, including, without limitation, growth factors and/or cells, including cultured cells.

The invention also discloses a method of enhancing binding of molecules, such as, for example, growth factors and cell cultures by applying ex vivo an effective quantity of an ionic force change agent to a bone graft structure, in particular, the surface of a bone graft structure, to produce a binding-sensitized bone graft structure, and implanting the binding-sensitized bone graft structure. An effective amount of molecules, including growth factors and cell cultures can be administered to the binding-sensitized bone graft structure both before and after implanting the modified bone graft into the host bone.

In another aspect, the invention involves the addition of an ionic force change agent to the bone graft structure thereby modifying its charge in a targeted manner to produce an appropriately charged bone graft structure. The ionic force change agent may be applied to the entire bone graft structure or to selected portions thereof. Additionally, the practitioner may optionally administer an appropriate molecule or cell culture. Generally, the molecule or cell culture is applied within minutes, for example from about 1 to about 120 minutes before implantation into the patient.

One class of molecules suitable for one embodiment of the invention is growth factors. Growth factors suitable for use in the practice of the invention include but are not limited to bone morphogenic proteins, for example, BMP-2, rhBMP-2, BMP-4, rhBMP-4, BMP-6, rhBMP-6, BMP-7[OP-1], rhBMP-7, GDF-5, and rhGDF-5, as disclosed, for example, in the U.S. Pat. Nos. 4,877,864; 5,013,649; 5,661,007; 5,688,678; 6,177,406; 6,432,919; 6,534,268, and 6,858,431, and in Wozney, J. M., et al. (1988) *Science,* 242(4885):1528-1534. Bone morphogenic proteins have been shown to be excellent at growing bone and there are several products being tested. Extensive animal testing has already been undertaken, and human trials are finished and in process for these products. rhBMP-2 delivered on an absorbable collagen sponge (INFUSE® Bone Graft, Medtronic Sofamor Danek, Memphis, Tenn.) has been used inside titanium fusion cages and resulted in fusion in 11 out of 11 patients in a pilot study and 99% of over 250 patients in a pivotal study. In July, 2002 INFUSE® Bone Graft received FDA approval for use in certain types of spine fusion. A pilot study with BMP-2 delivered on a ceramic carrier was recently published and reported a 100% successful posterolateral fusion rate. BMP-7 (OP-1) has reported 50-70% successful posterolateral lumbar fusion results in human studies to date. On May 4, 2004, INFUSE® Bone Graft was approved for acute, open fractures of the tibial shaft (Bosse et al. *NEJM* 347(24): 1924-1931, 2002; Govender et al. *JBJS* 84(12): 2123-2134, 2002). Studies with these and other BMP's are underway. However, it is important to note that use of BMP's may add cost to an already very expensive operation.

Additionally, suitable growth factors include, without limitation, LIM mineralization protein, platelet derived growth factor (PDGF), transforming growth factor β (TGF-β), insulin-related growth factor-I (IGF-I), insulin-related growth factor-II (IGF-II), fibroblast growth factor (FGF), beta-2-microglobulin (BDGF II), as disclosed in the U.S. Pat. No. 6,630,153.

Further, molecules which do not have growth factor properties may also be suitable for this invention. An example of such molecules is tartrate-resistant acid phosphatase.

In one embodiment, the bone graft structure is treated with a negatively-charged ionic force change agent to produce a negatively-charged bone graft structure. The negatively-charged bone graft structure attracts a positively charged molecule having a pI from about 8 to about 10. Examples of positively charged molecules having a pI from about 8 to about 10 include but are not limited to, rhBMP-2 and rhBMP-6.

In another embodiment, the bone graft structure is treated with a positively-charged ionic force change agent such that the positively-charged bone graft structure attracts a molecule with a slightly negative charge, for example a charge of pI about 5 to about 7. Examples of molecules having a slightly negative charge include rhBMP-4.

In yet another embodiment, the bone graft structure is treated with a positively-charged ionic force change agent to produce a positively-charged bone graft structure such that cells, in particular cell cultures having a negative surface charge bind to the positively-charged bone graft structure. Examples of cells which are suitable for use in the practice of the invention include but are not limited to mesenchymal stem cells, pluripotent stem cells, embryonic stem cells, osteoprogenitor cells and osteoblasts.

The mechanisms by which a bone graft structure may acquire ionic forces include but are not limited to ionization, ion adsorption and ion dissolution.

In one embodiment, the implant is modified to give it the selected charge by a one-to-one substitution of the calcium ion with lithium, sodium, potassium or cesium of hydroxyapatite.

In yet another aspect, treatments with gradient-affecting elements, such as elements present in hydroxapatite, and human proteins are employed. Suitable gradient-affecting proteins are those present in the organic phase of human bone tissue. The gradient-affecting proteins derive molecule or cell attraction without the potential damaging effects on the implants, as may be the case with other chemical treatments. Usually this is accomplished through surface treatments such as, for example, plasma treatment to apply an electrostatic charge on bone.

The term "plasma" in this context is an ionized gas containing excited species such as ions, radicals, electrons and photons. (Lunk and Schmid, Contrib. *Plasma Phys.*, 28: 275 (1998)). The term "plasma treatment" refers to a protocol in which a surface is modified using a plasma generated from process gases including, but not limited to, $O_2$, He, $N_2$, Ar and $N_2O$. To excite the plasma, energy is applied to the system through electrodes. This power may be alternating current (AC), direct current (DC), radiofrequency (RF), or microwave frequency (MW). The plasma may be generated in a vacuum or at atmospheric pressure. The plasma can also be used to deposit polymeric, ceramic or metallic thin films onto surfaces (Ratner, Ultrathin Films (by Plasma deposition), 11 *Polymeric Materials Encyclopedia* 8444-8451, (1996)). Plasma treatment is an effective method to uniformly alter the surface properties of substrates having different or unique size, shape and geometry including but not limited to bone and bone composite materials.

Specific embodiments according to the methods of the present invention will now be described in the following non-limiting examples. Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

EXAMPLE 1

An oxygen plasma, containing ions, free radicals, electrons and other excited species was used to modify and create negative charge on the surfaces of bone plugs. The treatment was carried out in a bell jar reactor. Radio frequency (RF, 13.56 MHz) power was delivered through an arrangement of one powered and two grounded planar electrodes. Applied and reflected power was balanced using a matching network. Pressure was measured with a Baratron sensor placed between the reactor and the vacuum pump. The pressure was controlled with a throttle valve placed between the pressure sensor and the pump. Gasses were metered into the chamber with mass flow controllers.

Bone plugs were placed upright on a stainless steel tray on the powered electrode. The treatment chamber was pumped down to a base pressure of 7 mTorr. Oxygen gas was metered into the system with a flow rate of 10 sccm to an operating pressure of 600 mTorr. The reactor was allowed to equilibrate for 10 minutes. 300 Watts of RF power was applied to the system for 2 minutes. With the RF power off, the chamber was then brought up to atmospheric pressure. The bone plugs were turned upside down so that the surface that had been in contact with the tray would be exposed during a second plasma treatment. The chamber was then pumped down to base pressure and the treatment cycle was repeated to plasma treat all surfaces of the bone plugs. Samples were removed from the plasma reactor and placed in sterile packages.

The oxygen concentration (found by electron spectroscopy for chemical analysis "ESCA") was used to assess negative charge on the surface. Table 1 shows the results obtained for human bone plugs that were plasma treated using oxygen as process gas and by standing upright on the electrode. Consequently, if only one treatment is carried out in this orientation, the unexposed end may not benefit from any effects of the plasma. To test this theory and monitor any undesirable effects of multiple doses, the plugs were turned over and received a second treatment. The bottom and along the length of these samples were analyzed by ESCA and the results are compared in Table 1.

TABLE 1

| Number of Treatments | Area Sampled | C | N | O | F | Si | P | Ca |
|---|---|---|---|---|---|---|---|---|
| 0 | Length of human bone | 43.22 | 3.37 | 38.13 | nd | nd | 5.98 | 8.75 |
| 1 | Bottom of human bone | 46.00 | 2.86 | 35.93 | 0.43 | nd | 5.57 | 8.01 |
| 1 | Length of human bone | 12.97 | nd | 46.48 | 13.60 | 1.96 | 8.00 | 15.71 |
| 2 | Bottom of human bone | 9.67 | nd | 44.45 | 18.60 | 3.28 | 6.17 | 16.54 |
| 2 | Length of human bone | 7.70 | nd | 50.55 | 13.69 | 4.47 | 6.70 | 14.79 |
| 2 | Ovine bone | 13.07 | 0.61 | 52.69 | 6.84 | 3.45 | 8.17 | 13.98 |

ESCA atomic concentrations (in %) of human cortical bone following $O_2$ plasma treatment for points sampled on the bottom and long the length of the plugs that underwent 1 and 2 treatment cycles respectively.
Also shown is the surface composition of an ovine bone sample after plasma treatments, sterilization and shipping.
(nd—not detected).

The bottom of the sample that received one treatment displays values very similar to those obtained for the untreated human bone samples. The unexposed surface was not affected by the oxygen plasma treatment. In all other instances the carbon content was reduced and the oxygen increased. These results clearly indicate that RF plasma can be used to effectively increase the oxygen content and therefore the partial negative charge of the surface of bone.

EXAMPLE 2

Samples of bone powder/polymer/demineralized bone composite comprising 50% polylactide (PLA), 30% demineralized bone (<80 micron), and 20% bone particles (<80 micron) were used to investigate the effect of plasma treatment. The same conditions that were carried out for the bone plugs, as described in Example 1, were applied to the composite material and the result of the measurements of ESCA surface atomic concentrations for untreated and treated samples are shown in Table 2. These data show a modest increase in oxygen (and therefore partial negative charge) on the surface of the $O_2$ plasma treated composite samples.

TABLE 2

| Sample | C | N | O | P | Ca |
|---|---|---|---|---|---|
| As received composite | 60.94 | 3.18 | 33.45 | 0.97 | 1.45 |
| Plasma treated composite | 45.22 | 4.76 | 41.16 | 3.30 | 5.00 |

ESCA atomic concentrations (%) for as received and plasma modified polymer/bone composite material.

EXAMPLE 3

Sample Preparation

Ovine cortical bone cylinders (4 mm diameter and 5 mm height) were machined from cadaver tibias and metatarsals. After machining, the Surface demineralized bone sample groups were first immersed in 0.6 N HCl (EMD Chemicals, Inc., Gibbstown, N.J.) for 30 minutes with constant agitation and washed with water.

All bone constructs were washed in 0.5% (w/w) SDS (Bio-Rad Laboratories, Hercules, Calif.)/0.5% (v/v) Triton X-100 (Sigma-Aldrich Co., St. Louis, Mo.) for 120 minutes under vacuum and constant agitation, and washed with water. These constructs were placed into Chex-all II Instant Sealing Sterilization Pouches (Propper Manufacturing Co., Inc., Long Island City, N.Y.) and freeze dried (Freeze Dry System, Labconco Corporation, Kansas City, Mo.) for 48 hours. All bone cylinders were gamma irradiated (Nuteck Corporation, Hayward, Calif.) to simulate the terminal sterilization treatment of allograft bone commonly utilized at tissue banking facilities.

Oxygen vacuum plasma treatments were used to create negative charge on the surfaces of bone plugs. The treatment was carried out in a bell jar reactor. Bone plugs were placed upright on a stainless steel tray on the powered electrode. The treatment chamber was pumped down to a base pressure of 7 mTorr as measured with a Baratron sensor placed between the reactor and the vacuum pump. The pressure was controlled with a throttle valve placed between the pressure sensor and the pump. Oxygen gas was metered into the system with mass flow controllers at a flow rate of 10 sccm to an operating pressure of 600 mTorr. The reactor was allowed to equilibrate for 10 minutes. 300 Watts of Radio Frequency (RF, 13.56 MHz) power delivered through an arrangement of one powered and two grounded planar electrodes was applied to the system for 2 minutes. Applied and reflected power was balanced using a matching network. With the RF power off, the chamber was then brought up to atmospheric pressure. The bone plugs were turned upside down so that the surface that had been in contact with the tray would be exposed during a second plasma treatment. Plasma modified samples were removed from the plasma reactor and placed in sterile packages.

All groups (Untreated allograft, surface demineralized bone, straight pits (1 mm diameter×1 mm deep), undercut pits (1 mm deep with a surface diameter of 1 mm and an interior diameter of 1.5 mm), and cortical bone with a negative surface charge) were all examined in vivo with and without a biologically active compound. All groups without a bioactive compound (n=13) were inserted directly into the defect without hydration of the bone plugs. The groups receiving rhBMP-2 (n=13) had 500 µl of 0.43 mg/mL rhBMP-2 dripped onto the construct, and occasionally rolled in the resulting pool of rhBMP-2. After the 15-minute soak, the appropriate cortical allograft/rhBMP-2 construct was inserted into the defect. One group of straight pits (n=13) received 0.1 g of sheep DBM mixed with 20 µl warm saline (37° C.). The resulting paste was smeared across the surface of the straight pit construct prior to insertion into the defect.

Ovine Cortical Defect Model

Twenty (20) skeletally mature adult domestic sheep were assigned to one group corresponding to an implantation period of eight weeks post-operative. Animals were initially screened to exclude acute and chronic medical conditions, including Q-fever and Johne's disease, during a one-week quarantine period prior to surgery. Specific attention was paid to selecting animals of uniform size and weight to limit the variability of loading.

Phenylbutazone (1 g p.o.) and Cefazolin sodium were administered approximately 20 to 30 minutes prior to anesthesia induction. Induction of anesthesia was administered by intramuscular (IM) injection of examine (11 mg/kg) and xylazine (2 mg/kg). Following induction, anesthesia was maintained by endotracheal tube delivered isoflurane. The right hind leg was shaved and prepped with povidone-iodine solution, and draped in a sterile fashion.

A lateral approach to expose the right tibia and fused $3^{rd}$ and $4^{th}$ metatarsal was performed by blunt dissection. Four 4 mm diameter holes were drilled in each bone for a total of 8 implants per animal. The defect was irrigated with saline to remove bone particles or fragments prior to inserting the appropriate plug into the hole, flush with the host bone. A marking screw was inserted near the 2 defects at each end of the bone. Placement verification for post-mortem analyses was made by measuring the distance between the defect and the screw and noted on the animal's surgical sheet. The subcutaneous (SC) layer was closed with running suture, and the skin closed with staples.

Following the procedure, a Fentanyl patch was applied, and an additional dose of Cefazolin sodium was administered. Post-operative radiographs were obtained to obtain baseline densities within the defect and to verify placement.

The animals were not immobilized following surgery, and supplied chow and water ad lib. Animals were kept in recovery cages for several hours post-operatively after which they were transferred to standard cages so that motion was limited. After ten days, the animals were transferred to the off-site housing facility and allowed unrestricted motion in a naturalistic environment.

All animals were sacrificed eight weeks post-operatively using an intravenous barbiturate overdose. The overlying soft tissues will be sharply dissected from the defect site, the tibias and metatarsals examined for any gross deformities, and the operative section of the bones retrieved. Tibia and metatarsal bones from euthanized sheep were labeled and transported from necropsy to the Orthopaedic Bioengineering Lab (OBRL). The defects were identified by the intra-operative marking screw. Defects and surrounding bone were dissected using an Exakt Bone Saw (Exakt Technologies, Oklahoma City, Okla.). For defects undergoing biomechanical testing, 2 cm of host bone was retained; for histological specimens, 1 cm of bone surrounding the defect was retained.

Biomechanical Testing

Biomechanical Specimens were tested on the day of euthanasia. Specimens were placed on a custom fixture allowing orientation of the defect (allograft plug) to be perpendicular to the direction of load application. The testing fixture contained a support plate that supported the host bone surrounding the allograft plug. The clearance of the hole in the support jig was 0.7 mm (diameter of support plate hole=5.0 mm+1.4 mm=6.4 mm). A cylindrical pin with a flat loading surface (3.5 mm diameter) was used to push out the allograft plug. Using a servo-hydraulic testing system (MTS Bionix 858, Eden Prairie, Minn.), the pin applied a load to the allograft construct at a displacement rate of 2 mm/min with load and displacement data acquired at 100 Hz. Once the break load was reached, the test was stopped. Peak load was identified as the highest load prior to a significant drop (maximum force).

After the allograft construct was pushed out, the empty allograft plug hole was bisected with the Exakt Saw. Cortical bone thickness at the hole was measured with digital calipers. The engineering analyses of the biomechanical data were:

1) Ultimate Force     Maximum force $$\text{Shear Strength} = \frac{F}{\Pi \cdot D \cdot H}$$

-continued

2) Shear Strength wherein
F = Ultimate force
D = Outer diameter of cylindrical implant (4 mm in all cases)
H = Average transcortical bone interface thickness $$\text{Shear Modulus} = \frac{F(\ln R_2 - \ln R_1)}{2 \cdot \Pi \cdot d \cdot H}$$

3) Shear Modulus wherein
F = Ultimate force
$R_2$ = Radius of defect
$R_1$ = Radius of implant
d = Displacement at ultimate force
H = Transcortical interface length (as measured by digital calipers)

Using the combined data from two studies, the effects of allograft treatment on biomechanical properties (ultimate load, shear strength, and shear modulus) were determined using a one-way ANOVA. Effects of allograft treatment on histomorphometric parameters were analyzed for significance comparing only two groups at a time using the Parametric Unpaired t-test (two-tailed, P-value with 95% Confidence Intervals).

Ultimate load at failing was significantly greater for the Straight pits/rhBMP-2 group compared to the Negative surface charge, Untreated allograft, Negative surface charge/rhBMP-2, and Undercut pit groups ($p<0.05$). However, the importance of this biomechanical parameter is questionable and potentially misleading, as ultimate load measures alone can not adequately describe the mechanical integrity of the bone-graft interface. Mechanical integration or resistance to push out is better represented by shear strength and shear modulus measures since the contact area between the plug and the host cortical bone is both considered in the calculation as well as used to normalize these values, thus allowing direct comparison to the values to be more indicative of the true effect of the treatment groups. The shear strength for the Surface demineralized/rhBMP-2 and Straight pits/rhBMP-2 were approximately 30% and 25% higher than that for the Undercut pits, Untreated allograft/rhBMP-2, Undercut pits/rhBMP-2, Negative surface charge, and Negative surface charge/rhBMP-2 ($p<0.05$) respectively. Additionally, the shear strength was shown to be statistically greater for the Straight pits treatments compared to the Negative surface charge and Negative surface charge/rhBMP-2 treatments ($p<0.05$). A 50% improvement was seen in the shear modulus for the Surface demineralized/rhBMP-2 treatment group compared to Negative surface charge, Untreated allograft/rhBMP-2, Undercut pits/rhBMP-2, and Negative surface charge/rhBMP-2 ($p<0.05$). Many of the treatments were equivalent to Surface demineralized/rhBMP-2 including Straight pits/rhBMP-2, Straight pits, SDM, Untreated allograft, and Straight pits/DBM. However, Surface demineralized/rhBMP-2 consistently produced better interface mechanical properties than the other treatments.

The analysis also indicated trends showing that certain allograft treatments have adverse affects on the biomechanical properties. For the three biomechanical measured, the Undercut pit constructs had performance values below that of the Straight pit constructs. This is interesting because these treatments are similar except that the Undercut pits treatment had been undercut at depth to a diameter of 1.5 mm while the Straight pits had not. The biomechanical data implies the undercutting process has adverse effects. Further inspection also indicated a negative surface charge decreased the biomechanical performance of the allograft constructs. The shear strength and modulus data showed that the Negative surface charge and the Negative surface charge/rhBMP-2 treatments were statistically less then the top ranking constructs, as well as Untreated allograft.

Histological Analysis

The trimmed samples were fixed in 70% ethyl alcohol (ETOH) for 1 week. The specimens were dehydrated in graded solutions of ETOH (70%, 95%, and 100%) over the course of approximately 3 weeks with increasing concentrations of Technovit 7000 (embedding resin). The final solution contained 100% of the embedding resin which was polymerized using light activation. An average of 10 sections (7 µm thick) of each specimen was taken in the sagittal plane to include the implant and the adjacent bone. The sections were cut from the specimen block along the longitudinal axis of the defect using an Exakt diamond blade bone saw (Exakt Technologies, Okla., OK). All sections were ground flat using an Exakt microgrinder to 10-20 µm thickness. Sections were made at equal intervals. The sections were stained with a modified Van Gieson bone stain. Histological images were acquired using an Image Pro Imaging system (Media Cybernetics, Silver Spring, Md.) and a Nikon E800 microscope (AG Heinze, Lake Forest, Calif.), Spot digital camera (Diagnostic Instruments, Sterling, Heights, Mich.), and a pentium IBM-based IBM compatible computer with expanded memory capabilities (Dell Computer Corp., Round Rock, Tex.). Histomorphometric parameters measured included: Defect Area ($mm^2$), Bone Area within Defect Area ($mm^2$), Percent Bone Area within Defect (%), Graft Area within Defect Area ($mm^2$), and Percent Graft Area within Defect (%). Qualitative assessment of bone morphology and cellularity were made including: lamellar vs. woven bone, cellularity, inflammatory cells, and bone integration with graft material.

Graft resorption was increased by the addition of rhBMP-2, with the effects of this growth factor more evident at the endosteal region. Bone formation was also improved by the addition of rhBMP-2.

With the exception of the negative surface charge and Undercut pits/rhBMP-2 groups, all treatments had better de novo bone formation in the defect than Untreated allograft: Straight pits/rhBMP-2, Straight pits/DBM ($p<0.001$)>Untreated allograft/rhBMP-2, Surface demineralized/rhBMP-2, Straight pits, Negative surface charge/rhBMP-2, and Xenograft ($p<0.01$)>Undercut pits ($p<0.05$). Untreated allograft/rhBMP-2 was significantly better than Negative surface charge ($p<0.05$). Surface demineralized/rhBMP-2 was better than Undercut pits/rhBMP-2 ($p<0.05$) and Negative surface charge ($p<0.01$). Straight pits was better than Undercut pits/rhBMP-2 ($p<0.05$) and Negative surface charge ($p<0.05$). Straight pits/rhBMP-2 is better than Undercut pits ($p<0.01$), Undercut pits/rhBMP-2 ($p<0.01$), Xenograft ($p<0.01$), and Negative surface charge ($p<0.001$). Straight pits/DBM had significance over Undercut pits ($p<0.05$), Undercut pits/rhBMP-2 ($p<0.05$), Xenograft ($p<0.05$), and Negative surface charge ($p<0.001$). Negative surface charge/rhBMP-2 was significant over Undercut pits ($p<0.05$), Undercut pits/rhBMP-2 ($p<0.05$), Xenograft ($p<0.05$), and Negative surface charge ($p<0.01$). Xenograft was better than Negative surface charge ($p<0.01$).

The remaining histomorphometric analysis is presented in the groups in which they were originally analyzed: Group I (Untreated allograft, Surface demineralized, Surface demineralized/rhBMP-2, Straight pits, Straight pits/rhBMP-2, Straight pits/DBM, and Xenograft) and Group II (Untreated allograft/rhBMP-2, Undercut pits, Undercut pits/rhBMP-2, Negative surface charge, and Negative surface charge/rhBMP-2. In group I, significantly more graft remained in the defect for the Untreated allograft and Xenograft groups (p<0.005). The percent of de novo bone in the periosteal callus was significantly lower in the Untreated allograft group when compared to the other treatment groups (p<0.05). In group II, graft resorption within the defect was significantly improved for the Negative surface charge/rhBMP-2 group compared to the Negative surface charge group (p<0.05). There was greater graft resorption within the endosteal callus for all three treatments enhanced with rhBMP-2 compared to the two groups not exposed to the morphogen (p<0.05), except for Undercut pits which was not different than Undercut pits/rhBMP-2. All three rhBMP-2 treatment groups showed better de novo bone formation at the periosteal surface than the Negative surface charge treatment group (p<0.05). Negative surface charge/rhBMP-2 and Untreated allograft/rhBMP-2 had more de novo bone formation at the endosteal callus than the remaining treatment groups (p<0.05).

Histomorphometric results indicate that the addition of rhBMP-2 is responsible for an increase in bone de novo bone formation and a decrease on the amount of implanted allograft. In essence, treatments enhanced with growth factor stimulated new bone formation and also stimulated graft resorption. Osteoblastic stimulation was expected as a consequence of the addition of rhBMP-2 to the allograft plugs. However, osteoclasts, the cells responsible for bone and graft resorption, were also responsive to rhBMP-2.

Synopsis of histopathology is presented in Tables 3 and 4. An inflammatory reaction was only observed in the bovine xenograft sections. All treatments showed good incorporation of graft with host bone. Endosteal and periosteal graft incorporation was also observed for all treatments.

Allografts enhanced with rhBMP-2 showed better resorption than allograft alone, and rhBMP-2 seemed to aid osteoblasts activity. The results of the individual surface treatments were variable. Untreated allograft/rhBMP-2 showed the highest scores of bone remodeling, with the highest percentage of lamellar bone with allograft. Straight pits/DBM had the best cellular activity characterized by osteoclastic resorption of the graft, while straight pits/rhBMP-2 had the best osteoblastic new bone formation. Straight pits/rhBMP-2 showed the most consistent remodeling and allograft incorporation with large portions of the allograft plug remodeled. There was a more intense callus formation observed on the periosteal surface for undercut pits/rhBMP-2. Negative surface charge had the lowest scores for graft integration with host bone, and there was some fibrous tissue within the defect observed. Negative surface charge/rhBMP-2 showed the highest extension of graft resorption.

TABLE 3

Summary of histopathology results.

| Treatments | Allo Plug Present (Y, N) | Inflam Cells (0, 1, 2) | Allo Resorpt. (0, 1, 2, 3, 4) | Primary Allo Incorp Surface (E, P, B, H, A) | Allo Oclasts (0, 1, 2) | Allo Oblast (0, 1, 2) | New Bone Remodeling (0, 1, 2, 3) | Fibrous tissue Present in Defect (Y, N) |
|---|---|---|---|---|---|---|---|---|
| Allograft | y | 0.00 | 0.38 | h, x | 0.33 | 0.50 | 0.83 | y, n |
| Allograft/rhBMP-2 | y | 0.00 | 2.00 | p, b, h | 1.17 | 1.17 | 2.00 | n |
| Straight Pits | y | 0.00 | 1.67 | h, p, a, e | 1.17 | 1.33 | 1.17 | n |
| Straight Pits/rhBMP-2 | y | 0.00 | 2.38 | a, p, h | 1.38 | 2.00 | 1.13 | n |
| Straight Pits/DBM | y | 0.00 | 1.67 | a, h | 1.58 | 1.67 | 1.17 | n |
| Undercut Pits | y | 0.00 | 0.83 | p, h | 0.92 | 0.92 | 1.5 | n |
| Undercut Pits/rhBMP-2 | y | 0.00 | 2.2 | p, b, h | 1.2 | 1.2 | 1.8 | n |
| Surface demin. | y | 0.00 | 2.21 | a, h | 1.43 | 1.64 | 1.29 | n |
| Surface demin./rhBMP.2 | y | 0.00 | 1.88 | h, p | 1.38 | 1.50 | 1.50 | n |
| Neg. Surf. Charge | y | 0.00 | 1.33 | b, h | 0.83 | 0.83 | 1.33 | y (33.33%) |
| Neg. Surf. Charge/rhBMP-2 | y | 0.00 | 2.6 | p, b, h | 1.1 | 1.1 | 1.8 | n |
| Bovine Xenograft | y | 1.22 | 0.78 | h, a, e | 0.66 | 0.84 | 1.06 | n, y |

| Treatments | Integrat. Allo with Host (0, 1, 2) | Extension Allo plug (E, P, C) | Callus Descript. (0, E, P, B) | Largest Callus (E, P) | Endosteal Callus Size (0, 1, 2, 3, 4) | Periosteal Callus Size (0, 1, 2, 3, 4) | Callus Remodeling (0, 1, 2, 3) |
|---|---|---|---|---|---|---|---|
| Allograft | 0.33 | c | o, p | NA, p | NA, p | NA, 0.5 | NA, 1 |
| Allograft/rhBMP-2 | 0.00 | e, c | p, b | e, p | 1.17 | 1.67 | 1.67 |
| Straight Pits | 0.00 | c, e, p | p, e | p, e | 0.25 | 0.60 | 1.00 |

TABLE 3-continued

Summary of histopathology results.

| | | | | | | | |
|---|---|---|---|---|---|---|---|
| Straight Pits/ rhBMP-2 | 0.00 | c | p, b | p | 0.13 | 0.63 | 1.00 |
| Straight Pits/DBM | 0.00 | c, e | b, e, p | e, p | 0.67 | 0.58 | 1.00 |
| Undercut Pits | 0.00 | e | 0, e, p | e, p | 0.33 | 0.33 | 1.50 |
| Undercut Pits/ rhBMP-2 | 0.00 | e | p, b | p | 0.8 | 1.80 | 1.80 |
| Surface demin. | 0.00 | c, e | b, p, e, x | p, e | 0.50 | 0.42 | 1.33 |
| Surface demin./ rhBMP.2 | 0.00 | e, c | 0, p, b | p, e, NA | 1.00 | 0.75 | 1.00 |
| Neg. Surf. Charge | 0.67 | e | 0, e, p | e, p | 0.33 | 0.33 | 1.50 |
| Neg. Surf. Charge/ rhBMP-2 | 0.00 | e, p | p, b | e, p | 1.00 | 1.60 | 1.80 |
| Bovine Xenograft | 0.13 | e, x, c | 0, b, p, x | p, e | 0.43 | 0.53 | 1.00 |

Histopathological analyses also revealed that the addition of rhBMP-2 stimulates de novo bone formation, bone remodeling, allograft incorporation and cellular activity. More exuberant callus tissue was also observed for the treatments enhanced with the rhBMP-2. Additionally, the histology showed that callus formation was more substantial on the periosteal surface. This was probably due to the graft usually being inserted all the way into the medullary cavity; thus, the periosteal surface of the graft was often leveled with host bone, while the endosteal surface was frequently protruding into the medullary cavity.

TABLE 4

Summary of histopathology analysis for each treatment.

| Treatment | Comments |
|---|---|
| Untreated allograft | Minimal incorporation mostly originating from the graft-host interface. Minimal remodeling. Graft appears to be inert. |
| Untreated allograft/rhBMP-2 | Allograft included in all sections. No inflammatory reaction present. Graft resorbed to some extent. Moderate cellular activity was accompanied by excellent new bone remodeling. Periosteal callus was more evident compared to endosteal callus. Woven and lamellar bone was similarly observed in the healing callus. |
| Surface demineralized | Variable response. Some plugs appear to have extensive remodeling and plug resorption; whereas, others have activity limited to the surface of the allograft. In general, active bone formation and remodeling was observed in all sections. |
| Surface demineralized/ rhBMP-2 | Variable response. Half of the sections show great resorption of the graft and the other half show minimal allograft resorption. All plugs show excellent integration and active remodeling. |
| Straight pits | Variable response. Some plugs appear to have extensive remodeling; whereas, others have activity limited to the surface of the pits. In general, active bone formation and remodeling occurred at the pits. |
| Straight pits/rhBMP-2 | Great remodeling and plug incorporation. Osteoblast actively was impressive. Large portion of the plug remodeled. |
| Straight pits/DBM | Response was variable. Some specimens had great plug resorption and remodeling; whereas, others were well integrated, especially in the pits, but not good resorption. In general, good remodeling and activity. |
| Undercut pits | Allograft present in all specimens. Very little bone activety observed. Inflammatory cells were not detected. Endosteal and periosteal callus present in 2 of 6 specimens. Minimal graft resorption. |
| Undercut pits/rhBMP-2 | Allograft was present in all specimens. No inflammatory reaction observed. Some graft resorption detected. Good osteoblastic and osteoclastic activity accompanied by moderate new bone remodeling. Periosteal callus more evident than endosteal callus formation, consisting, of mainly, lamellar bone. |
| Negative Surface Charge | Allograft present in all specimens. Minimal bone remodeling with presence of endosteal or periosteal callus in 2 of 6 specimens. Graft resorption was observed to some extent. Fibrous tissue was present in 2 of 6 specimens compromising host-graft integration. No inflammatory reaction detected |

TABLE 4-continued

Summary of histopathology analysis for each treatment.

| Treatment | Comments |
| --- | --- |
| Negative Surface Charge/rhBMP-2 | Allograft included in all sections. Two of 6 specimens presented graft into periosteal surface. No inflammatory reaction present. Intense graft resorption observed. Moderate cellular activity, and moderate new bone remodeling was present. Callus formation was more evident on the periosteal side with primarily lamellar bone observed. |
| Bovine Xenograft | Inflammatory cells present. Most integration coming from the host bone. Remodeling evident, yet limited in scope. |

Undercut pits/rhBMP-2 specimens were frequently graded as having excellent callus formation with intense cellular activity, and very good callus maturity. Negative surface charge/rhBMP-2 specimens demonstrated the best graft resorption, and also established adequate callus maturity. Undercut pits or negative surface charged specimens without rhBMP-2 had inferior bone healing, with minimal cellular activity, graft resorption and callus formation.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

We claim:

1. A method for enhancing ingrowth of host bone comprising: modifying at least two surfaces of a bone graft structure by plasma treating the at least two surfaces so as to impart a negative charge to the at least two surfaces to produce a modified bone graft structure; and implanting the modified bone graft structure, wherein a growth factor is administered to the modified bone graft structure, the growth factor having a pI of between about 8 and about 10.

2. The method of claim 1, wherein the bone graft structure is surface demineralized and a cell culture is administered to the modified bone graft structure.

3. The method of claim 2 wherein the cell culture is selected from the group consisting of mesenchymal stem cells, periosteal cells, pluripotent stem cells, embryonic stem cells, osteoprogenitor cells, osteoblasts, osteoclasts, bone marrow-derived cell lines, and any combination thereof.

4. The method of claim 1, wherein the plasma comprises oxygen plasma.

5. The method of claim 1 wherein the bone graft structure is selected from the group consisting of cortical bone, cancellous bone, subchondral bone and any combination of the various bone tissue types.

6. The method of claim 5, wherein the bone graft structure consists of cortical bone.

7. The method of claim 1, wherein the bone graft structure comprises a composite bone.

8. The method of claim 7, wherein the composite bone comprises a bone powder, and demineralized bone particles.

9. The method of claim 1 wherein (i) the growth factor is selected from the group consisting of BMP-2, rhBMP-2, BMP-4, BMP-6, rhBMP-6, BMP-7, rhBMP-7, GDF-5, LIM mineralization protein, platelet derived growth factor (PDGF), transforming growth factor β (TGF-β), insulin-related growth factor-I (IGF-I), insulin-related growth factor-II (IGF-II), fibroblast growth factor (FGF), and beta-2-microglobulin (BDGF II), rhGDF-5, or (ii) a tartrate-resistant acid phosphatase is administered to the modified bone graft structure.

10. A method of enhancing binding of a growth factor to a bone graft structure comprising: applying ex vivo an effective quantity of plasma to at least two surfaces of a bone graft structure to impart a negative charge to the at least two surfaces to produce a binding-sensitized bone graft structure, implanting said binding-sensitized bone graft structure into a host bone; and administering to said at least two surfaces a growth factor having a pI of between about 8 and about 10.

11. The method of claim 10, wherein the bone graft structure is surface demineralized.

12. The method of claim 10 wherein the plasma comprises oxygen plasma.

13. The method of claim 10 wherein the growth factor comprises rhBMP-2.

14. The method of claim 10 wherein the growth factor is selected from the group consisting of BMP-2, rhBMP-2, BMP-4, BMP-6, rhBMP-6, BMP-7, rhBMP-7, GDF-5, LIM mineralization protein, platelet derived growth factor (PDGF), transforming growth factor β (TGF-β), insulin-related growth factor-I (IGF-I), insulin-related growth factor-II (IGF-II), fibroblast growth factor (FGF), beta-2-microglobulin (BDGF II), and rhGDF-5.

15. The method of claim 10 wherein a cell culture is administered to the binding-sensitized bone graft structure and the cell culture is a culture of cells selected from the group consisting of mesenchymal stem cells, periosteal cells, pluripotent stem cells, embryonic stem cells, osteoprogenitor cells, osteoblasts, osteoclasts, and any bone marrow-derived cell lines.

16. The method of claim 10, wherein a tartrate-resistant acid phosphatase is added to the binding-sensitized bone graft structure.

17. The method of claim 10 wherein the bone graft structure is selected from the group consisting of cortical bone, cancellous bone, subchondral bone and any combination of the various bone tissue types.

18. The method of claim 17, wherein the bone graft structure consists of cortical bone.

19. The method of claim 10, wherein the bone graft structure comprises a composite bone.

20. The method of claim 19, wherein the composite bone comprises a bone powder, and demineralized bone particles.

* * * * *